United States Patent [19]
LeVeen et al.

[11] Patent Number: 5,810,755
[45] Date of Patent: Sep. 22, 1998

[54] MEDICATED WOUND DRESSING

[76] Inventors: Harry H. LeVeen, Charleston, S.C.; Mary Louise LeVeen, 2173 St. James Dr., Charleston, S.C. 29412, legal representative of said Harry H. LeVeen, deceased; Eric G. LeVeen, 19 Palmetto Rd., Charleston, S.C. 29407; Robert F. LeVeen, 815 S. 94th St., Omaha, Nebr. 68114

[21] Appl. No.: 710,229

[22] Filed: Sep. 12, 1996

Related U.S. Application Data

[63] Continuation-in-part of Ser. No. 324,471, Oct. 17, 1994, abandoned.

[51] Int. Cl.$^6$ ....................................................... A61F 13/00
[52] U.S. Cl. ........................... 602/48; 602/46; 604/890.1; 604/265; 424/447; 424/448
[58] Field of Search ................................. 602/42, 43, 46, 602/48, 53, 54, 56, 58, 59; 604/304, 306, 307, 265, 890.1, 891.1, 892.1; 128/846–847, 849, 888; 424/445–449

[56] References Cited

U.S. PATENT DOCUMENTS

| | | | |
|---|---|---|---|
| 4,226,232 | 10/1980 | Spence | 602/48 |
| 4,340,043 | 7/1982 | Seymour | 128/849 |
| 4,381,380 | 4/1983 | Leveen et al. | 604/265 |
| 4,588,400 | 5/1986 | Ring et al. | 602/48 |
| 4,728,323 | 3/1988 | Matson | 602/48 |
| 4,762,124 | 8/1988 | Kerch et al. | 602/48 |
| 5,000,749 | 3/1991 | LeVeen et al. | . |
| 5,010,883 | 4/1991 | Rawlings et al. | 602/52 |
| 5,070,889 | 12/1991 | LeVeen et al. | . |
| 5,115,801 | 5/1992 | Cartmell et al. | 602/48 |
| 5,156,164 | 10/1992 | LeVeen et al. | 604/890.1 |
| 5,330,452 | 7/1994 | Zook | 602/48 |
| 5,415,866 | 5/1995 | Zook | 424/448 |
| 5,419,913 | 5/1995 | Podell et al. | 602/48 |
| 5,437,621 | 8/1995 | Andrews et al. | 602/42 |
| 5,462,743 | 10/1995 | Turner et al. | 424/448 |
| 5,487,889 | 1/1996 | Eckert et al. | 424/93.1 |
| 5,501,661 | 3/1996 | Cartmell et al. | 602/58 |
| 5,505,958 | 4/1996 | Bello et al. | 602/46 |
| 5,620,702 | 4/1997 | Podell et al. | 424/448 |

OTHER PUBLICATIONS

LeVeen et al., *The Mythology of Providone–Iodine and the Development of Self Sterilizing Plastics,* Surgery, Gynecology & Obstetrics, Feb. 1993, vol. 176, pp. 183–190.

*Primary Examiner*—Michael Powell Buiz
*Assistant Examiner*—Chalin Smith
*Attorney, Agent, or Firm*—Herbert F. Ruschmann; Lawrence W. Wechsler

[57] ABSTRACT

A wound dressing, suitable for use in protecting an open wound or burned tissue from direct exposure to air and capable of maintaining an aqueous environment of wounded tissue with which it is in brought into contact is comprised of a hydrophilic, yet insoluble material, advantageously a polymeric compound capable of being reversibly complexed with elemental iodine, thereby permitting release of therapeutic amounts of free iodine into a wound with which it is brought in contact. As a shaped mass of pliable and absorbent material, such a polymeric foam, such dressing is particularly suited for application to fresh and infected burns and open wounds. When alternatively configured as a hydrophilic film complexed with free iodine for use as a surgical drape, in addition to providing a barrier against direct exposure to air, such dressing is bacteriocidal, preventing infection of the wound from airborne contaminants in the operating room.

20 Claims, 2 Drawing Sheets

MEDICATED WOUND DRESSING

REFERENCE TO RELATED APPLICATION

This application is a continuation-in-part of application Ser. No. 08/324,471 filed Oct. 17, 1994 entitled A WOUND DRESSING, now abandoned.

BACKGROUND OF THE INVENTION

The incidence of infection of wounds is generally dependant upon the causative factors, and the type and extent of damage to the skin. Wounds resulting from accidental causes are exposed to environmental contaminants, and are therefore invariably subject to later infection. When such injury occurs outdoors, these so called "dirty wounds" are particularly prone to infection because of the high level of contamination. When wounds are denuded of overlying skin there is an additional tendency towards infection from airborne contamination. When a significant amount of underlying tissue is exposed, a risk of infection may exist even in clean environments, such as operating rooms.

It has been shown that the incidence of infection, even in clean operative wounds, is directly proportional to the length of time that the tissues are exposed to air. Drying of the tissue during long periods of exposure devitalizes it, lowering resistance of the contaminated tissue to infection. Another factor detrimental to the healing of open wounds, is the loss of carbon dioxide to the air from the wound's surface. Such loss produces a respiratory alkalosis in the local tissue, leading to an alkaline shift in the pH. This results in an undesirable shift of the hemoglobin/oxyhemoglobin dissociation curve, which in turn stabilizes the oxyhemoglobin, and inhibits its conversion to reduced hemoglobin at reduced oxygen tensions (known as the Bohr effect). Thus, as noted in an article by LeVeen, H. et al., Ann Surg 148: pp 745–753(1973), incorporated herein by reference for its relevant teachings regarding this effect, wounds are desirably maintained at a relatively acid pH, whereby the oxygen tension is raised.

Various products have been developed, intended to discourage infection when topically applied. Antibiotics, and preparations containing silver salts or sulfonamide compounds, for example, have been used with some success. However, some wounds, for example those the result of burns, often become infected notwithstanding such preventative application. Various prior art wound dressings have also been developed to address the need to prevent wound infection, but have not heretofore demonstrated the required effectiveness.

Iodine has been used advantageously to treat wounds and prevent infection, by virtue of its germicidal, algaecidal, sporicidal, amoebacidal, myocidal, virucidal and bacteriocidal properties. To be effective, however, treatment of the wound or burn with iodine must continue essentially uninterrupted, heretofore requiring continual and repeated application of the iodine to the wound site at regular intervals.

During surgery, exposure to airborne contaminants is a problem contributing to infection of the patient, particularly during such procedures as vascular grafts, in which there is evidence that contamination often occurs to the exposed tissues of the skin during preparation of the graft. Sterile drapes, for example of the type offered by 3M Corporation under the trade name IOBAN, are presently used as a type of wound dressing, to cover wound sites during surgical procedures. These drapes are generally comprised of a film material, and are coated on the wound contact side thereof with a contact cement which may contain iodine. The iodine, so contained in the contact cement, is not transferable through the film barrier, and therefore does not offer the necessary protection from airborne contaminants.

It is known that free, or elemental iodine in concentrations of as low as one part per million (1 ppm) is sufficient to kill many bacteria. It has been shown clinically, for example, that a saline flush containing 2 ppm of free iodine was sufficient to prevent peritonitis in patients receiving peritoneal dialysis as a treatment for renal failure. Stephen RL et al., *Dialysis and Transplant,* 1979, 8:pp 584–655. An iodine/saline flush has also proved curative in other cases of peritonitis not related to dialysis. Furthermore, in these concentrations, iodine has been shown to be non-irritating, even when placed directly in the eye in the form of a 2 ppm iodine/saline wash. Id.

These authors, Stephen et al., state that the saline washed away glucose which would otherwise tend to convert free iodine to inactive iodine. Subsequent studies have indicated that rather than the 2 ppm shown effective in a saline solution, a higher concentration of between about 5 and 10 ppm of free iodine is believed to be required where glucose and protein are not flushed away. In such concentration, the iodine has been found to be bacteriocidal, virucidal, and fungicidal, and non-inflammatory and non-irritating to tissue.

Use of a lightly cross-linked polyurethane which has been complexed with free iodine has been suggested as a means by which iodine may be released in therapeutic concentrations when exposed to an aqueous environment. Known as a type of iodophor, use of such iodine complexed polyurethane is disclosed in U.S. Pat. No. 4,381,380 issued to LeVeen et al., and for purposes of rendering objects made from the material bacteriocidal, virucidal, and fungicidal.

Further U.S. Pat. Nos. 5,000,749, 5,070,889, and 5,156, 164 issued to LeVeen et al., expanded the use of such an iodophor to treating external tissue. As disclosed therein, an open cell polyurethane sponge was shown effective in treating and preventing vaginitis when complexed with iodine and used as a tampon. However effective in treating undamaged external tissue, the prior art does not offer guidance on the effectiveness or negative indications of using such an iodophor in direct contact with an open wound or burn.

It would therefore be desirable to provide a wound dressing, suitable for use in protecting an open wound or burned tissue from direct exposure to air for the reasons described above, and which is capable of maintaining an aqueous environment, permitting the release of medicants, including antiseptics such as iodine, into the wounded tissue with which it is in contact. When configured and used as a surgical drape, in addition to providing a barrier against direct exposure to air, such dressing would also be bacteriocidal, preventing infection of the wound from airborne contaminants in the operating room.

SUMMARY OF THE INVENTION

Accordingly, it is an object of the invention to provide a wound dressing which overcomes the drawbacks of the prior art.

It is a further object of the invention to provide a wound dressing which protects wounds, including those resulting from burns, from infection, by preventing drying at the protected site, and by maintaining the wound at a relatively acid pH.

It is a still further object of the invention to provide a wound dressing which is hydrophilic, and which is capable of releasing therapeutically effective amounts of free iodine to the wound over prolonged periods.

It is yet a further object to provide a wound dressing which may be replenished when medicants contained therein are depleted, without requiring removal from contact with the wound.

Briefly stated, the present invention provides a wound dressing comprised of a of hydrophilic, yet insoluble material, advantageously a polymeric compound capable of being reversibly complexed with elemental iodine, thereby permitting release of therapeutic amounts of free iodine into a wound with which it is brought in contact. Such polymeric compound may include such substances as polyurethane or other plastics, for example those which are the result of cross-linking polyalcohols. Such alcohols, include for example, glycerol, and other polyalcohols of high molecular weight, such as polyvinyl alcohol (PVA) polymers and cellulose polymers. Polyvinyl alcohol polymers are water soluble at all commercially available molecular weights from 25,000 to 100,000 and can be easily cross-linked to any desired molecular size and degree. By lightly (i.e. partially) cross-linking the polyalcohols, the resultant compound is hydrophilic, and retains reversible binding sites to which iodine may attach and be complexed therewith. PVA is easily cross-linked with a suitable cross-linking agent, including, for example, formaldehyde, glyoxal, glutaraldehyde, or diisocyanate, to form water insoluble compounds of high molecular weight. The dressing will generally be of a flattened and pliable, bandage-like configuration, although the precise physical characteristics, including size, shape, thickness, flexibility, etc. will depend upon the particular nature and extent of the wound, and its position on the body. Additionally, the wound dressing will include a non-irritating surface along a portion of its external surface which is specifically intended to come in direct contact with the wound, referred to herein as the "contact surface". In accordance with an embodiment of the invention, a wound dressing is comprised of a shaped mass of absorbent material, conveniently a non-irritating, hydrophilic, open cell foam. The foam or other suitable absorbent material is advantageously capable of complexing with iodine, and has reversible binding sites which permit release of therapeutically effective amounts of iodine into an aqueous environment. The material may be, for example, polyurethane, or a partially cross-linked polyalcoholic foam, as described above, or any other suitable material demonstrating the aforementioned desired properties. When placed in contact with a wound, the absorbent material serves to absorb fluids exuded from the injured tissue, keeping the covered wound moist, while continually releasing iodine into the wound in quantities that are bacteriocidal, yet non-irritating.

In a further embodiment directed primarily to treatment of wounds in which the tissue will remain open for prolonged periods, the wound dressing comprised of the absorbent material as described above is optionally covered with a film on a surface portion of the wound dressing not in contact with the wound site, referred to herein as the "outwardly facing surface". The film is advantageously impermeable to fluids, particularly aqueous fluids, to inhibit fluid loss to the ambient surroundings, and prevent soiling of the dressing by environmental contaminants. Where the absorbent material is a polyurethane foam, the film is advantageously a type bondable thereto.

In another embodiment, means are provided on the wound dressing which permit the infusion of medicants into the shaped absorbent mass to replace those depleted during use, without requiring removal of the dressing from the wound site. This feature is conveniently provided in the form of an enclosed envelope structure comprised of film, disposed on the surface portion of the wound dressing which is outwardly disposed when the dressing in contact with the wound. The envelope film, attached to and in direct overlaid contact with the absorbent material, is permeable to fluids, by virtue, for example, of perforations formed therein. The remaining film forming the envelope structure and not in direct contact with the shaped mass of the dressing is fluid impermeable, such that when a medicant is instilled into the envelope which serves as a reservoir, it seeps into the absorbent dressing material through the fluid permeable film layer interposed between the shaped mass and the outermost fluid impermeable film layer, replacing medicants, such as iodine, passing from the dressing into the wound.

In yet another embodiment, the wound dressing is in the form of a surgical drape, comprised of a hydrophilic film, and which may be adhered to skin to prevent contamination from airborne contaminants in, for example, an operating room. Such a drape would be comprised of polyurethane film, or other suitable film substance capable of reversibly complexing with elemental iodine.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
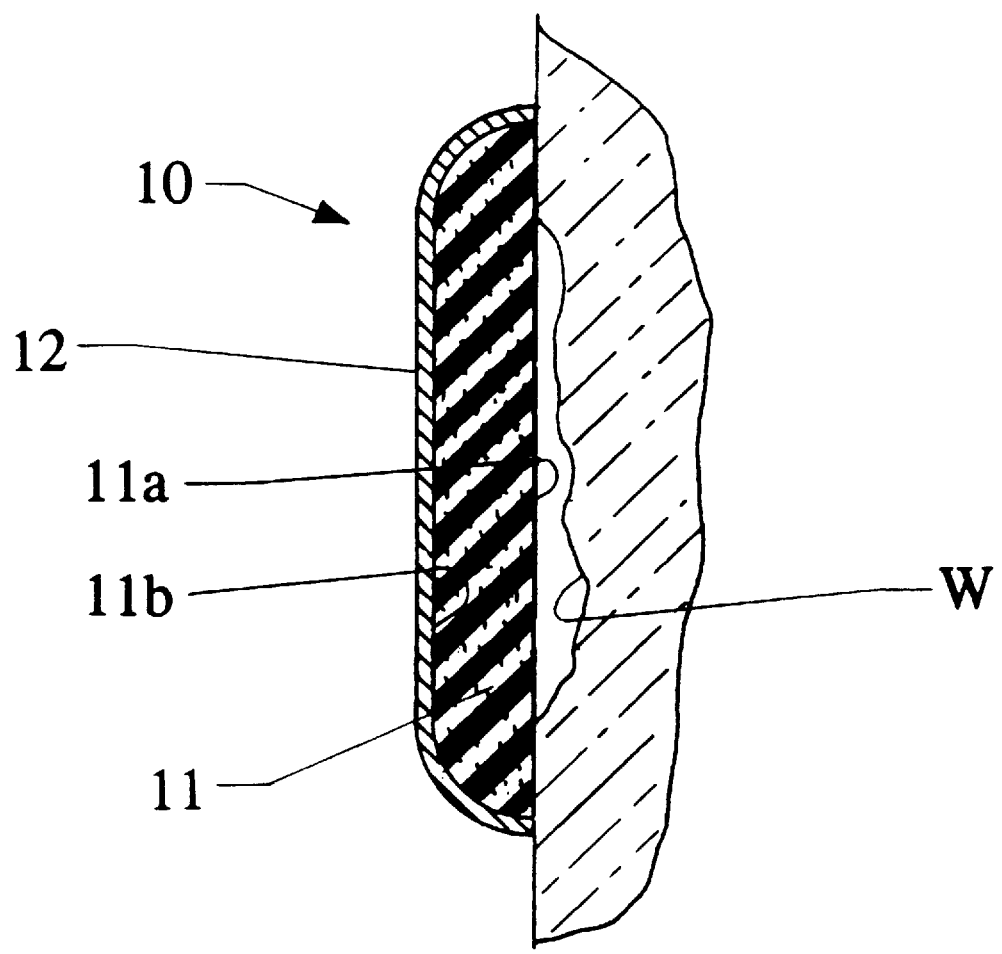
FIG. 1 is a side cross-sectional view of an embodiment of a wound dressing in accordance with the invention particularly suited for prolonged use.

The present invention provides a wound dressing comprised of a hydrophilic, yet insoluble material, advantageously a polymeric compound capable of being reversibly complexed with elemental iodine, thereby permitting release of therapeutic amounts of free iodine into a wound with which it is brought in contact. Such polymeric compound may include such substances as polyurethane or other plastics, for example those which are the result of cross-linking polyalcohols. Such alcohols, include for example, glycerol, and other polyalcohols of high molecular weight, such as polyvinyl alcohol (PVA) polymers and cellulose polymers. Polyvinyl alcohol polymers are water soluble at all commercially available molecular weights from 25,000 to 100,000 and can be easily cross-linked to any desired molecular size and degree. By lightly (or partially) cross-linking the polyalcohols, the resultant compound is hydrophilic, and retains reversible binding sites to which iodine may attach and be complexed therewith. PVA is easily cross-linked with a suitable cross-linking agent including for example formaldehyde, glyoxal or glutaraldehyde to form water insoluble compounds of high molecular weight. The precise physical characteristics, including size, shape, thickness, flexibility, etc. will depend upon the nature and extent of the wound, and its position on the body. In general, however, such wound dressing will include a non-irritating surface along a portion of its external surface which is specifically intended to come in direct contact with the wound and surrounding tissue, referred to herein as the "contact surface". Also for purposes herein, the remaining external surface not intended to contact the patient will be referred to as the "outwardly facing surface".

In accordance with an embodiment of the invention, a wound dressing is provided in the form of a shaped mass, conveniently comprised, for example, of a non-irritating, hydrophilic, open cell foam. Regardless of the material selected for the shaped mass, the material should advantageously be absorbent, pliable and present a wound contact surface which is non-irritating to the wound site with which it is to be brought in contact. The material should also advantageously be capable of complexing with iodine, and contain reversible binding sites which permit release of therapeutically effective amounts of iodine into an aqueous environment. Studies conducted in conjunction herewith have indicated that the incidence of infection can be sharply reduced or prevented in contaminated open wounds, even those containing devitalized tissue, by the application, advantageously immediately following the time of injury or as soon thereafter as permitted, of such iodine complexed dressing, thus advancing the concept of employing a complexed iodophor for its bacteriocidal properties, to treatment of open wounds and burns.

The material from which a suitably shaped dressing is fabricated may be, for example, polyurethane, or a partially cross-linked polyalcoholic foam, as outlined above, or any other suitable material demonstrating the aforementioned desired properties. It is further noted that although an open cell foam is conveniently employed, other suitable material exhibiting like properties mentioned as advantageous to the invention may be substituted without departure from the intended scope herein. For example, the shaped mass may be a fibrous or woven pad made of the aforementioned materials or other suitable compounds. When placed in contact with a wound, the dressing material advantageously serves to absorb fluids exuded from the injured tissue, keeping the covered wound moist, while continually releasing iodine into the wound in quantities that are bacteriocidal, yet non-irritating. Detailed examples of suitable polyurethane compounds to be used for this embodiment and for any subsequently described embodiments herein which include an iodine complexed hydrophilic material for releasing therapeutically effective concentrations of iodine in an aqueous environment may be found in U.S. Pat. Nos. 4,381,380, 5,000,749, 5,070,889, and 5,156,164 issued to LeVeen et al., which are incorporated herein by reference for their teachings regarding the characteristics of the polyurethane foam, effective amounts of iodine, methods for complexing the foam dressing material with iodine, and any additional subject matter contained therein relevant to the invention disclosed herein.

As noted, in accordance with the above described embodiment of the invention, any material demonstrating suitable characteristics, for example, any hydrophilic, open celled foam capable of complexing sufficiently with iodine to release therapeutically effective concentrations of free iodine, may be used in addition to polyurethane foam. For example, a foamed solid hydrophilic polyalcoholic plastic can be complexed with iodine typically by immersion in an aqueous solution of iodine containing iodides. For purposes herein, it is generally desirable to select a foam or other suitable material which is insoluble in water but which demonstrates an affinity to water, i.e. hygroscopic characteristics. As already noted, PVA foams sparingly cross-linked with formaldehyde, diisocyanate or other suitable cross-linking agents, form polyalcoholic plastics which are water insoluble but very hygroscopic. While being water insoluble, these cross-linked compounds all retain a strong affinity for water. Like cellulose sponges commonly used in kitchens and bathrooms, most of these foams are rigid in their dry form in contrast to hygroscopic open cell polyurethane foams which remain soft and pliable in the dry state. Water, however, plasticizes them, making them soft and flexible. One such foam of lightly cross-linked PVA is commercially available, for example, as manufactured and sold under the trade name of Ivalon sponge for medical applications by Unipoint Industries, Inc., 120 Transit Avenue, Thomasville, N.C. 27360. PVA sponges have a great affinity for dissolving iodine. Such sponges can be iodinated, for example, by aqueous iodine solutions containing iodides such as Aqueous Iodine Solution (USP), which is a 2% solution of iodine in a 2.6% solution of sodium iodide. When PVA sponge is dipped into this iodine solution, the sponge turns dark purple. The sponge is then washed and compressed repeatedly in running deionized water to remove all traces of iodide and any excess iodine. The iodinated cross-linked PVA foams readily dissolve iodine and since iodine is relatively insoluble in water, (0.0013 moles of iodine dissolve in 1 liter of water at 25° C.) a partition coefficient is set up between the concentration of iodine in the sponge and the concentration of free iodine in the water. In addition, sulfates may be used to decrease the solubility of free iodine in water to non-irritating concentrations. This partition coefficient is proportional to the degree of loading in the sponge and can be adjusted to establish any desired initial free iodine concentration in body fluids, for example, by varying exposure time and concentration of immersion solution. We have found that a initial free iodine concentration between 5 and 50 parts per million to be ideal. However, in the presence of blood or protein this level can be safely adjusted to as high as 100 ppm. In the preferred case, such sponges are applied to wounds in their moistened form, containing physiological saline solution. (0.9% sodium chloride dissolved in distilled water). The dressing may be packaged in such moistened state, ready for application.

Regardless of what material is selected for the shaped mass of the dressing, complexing with iodine is accomplished in a like manner. As described above, iodine complexing may be typically accomplished, for example, by dipping the dressing in an aqueous iodine solution containing iodides such as Aqueous Iodine Solution (USP), which is a 2% solution of iodine in a 2.6% solution of sodium iodide. The foam or like material is immersed in this solution with compression to dispel any entrapped air. When fully saturated with the solution, the dressing is removed and again compressed to expel any residual iodine solution, and is then transferred to running deionized water and repeatedly compressed to purge any sodium iodide and unattached iodine. This is continued until the effluent is clear. The dressing is then air dried. For prolonged storage prior to use, the iodinated dressing described in the present and any subsequent iodine complexed embodiments may optionally be placed in a sealed, air-tight package to prevent sublimation which would otherwise occur due to the vapor pressure of iodine.

In a further embodiment, the shaped mass of the dressing is acidified by treatment with an organic polybasic acid or a polycarboxylated polyvinyl resin. This serves to advantageously raise the $pO_2$ of ischemic tissue, to promote healing. The dressing material may be so treated, for example, by placement in a 4% aqueous solution of such polycarboxylated polyvinyl resin, available for example from B. F. Goodrich under the trade name CARBOPOL. When such acidification of the dressing is performed in advance of application to the wound, and the resin allowed to dry in the shaped mass, the dressing material should be moistened with normal saline solution prior to application to the wound.

A further embodiment is directed primarily to treatment of wounds in which the tissue will remain open for prolonged periods. Referring to the figures, and in particular FIG. 1, a wound dressing as described in the preceding embodiments, generally designated 10, and shown in contact with a wound W, includes a shaped mass 11 presenting an exterior surface configuration comprised of a wound contact surface 11a and an outwardly facing surface 11b. Outwardly facing surface 11b, i.e. the external surface not brought into direct contact with the wound W or surrounding tissue, is covered with a film 12. Film 12 is advantageously impermeable to fluids, particularly aqueous fluids, to inhibit fluid loss to the ambient surroundings, and prevent soiling of shaped mass 11 by environmental contaminants. Where shaped mass 11 is a polyurethane foam, film 12 is advantageously a type bondable thereto.

Figure 2:
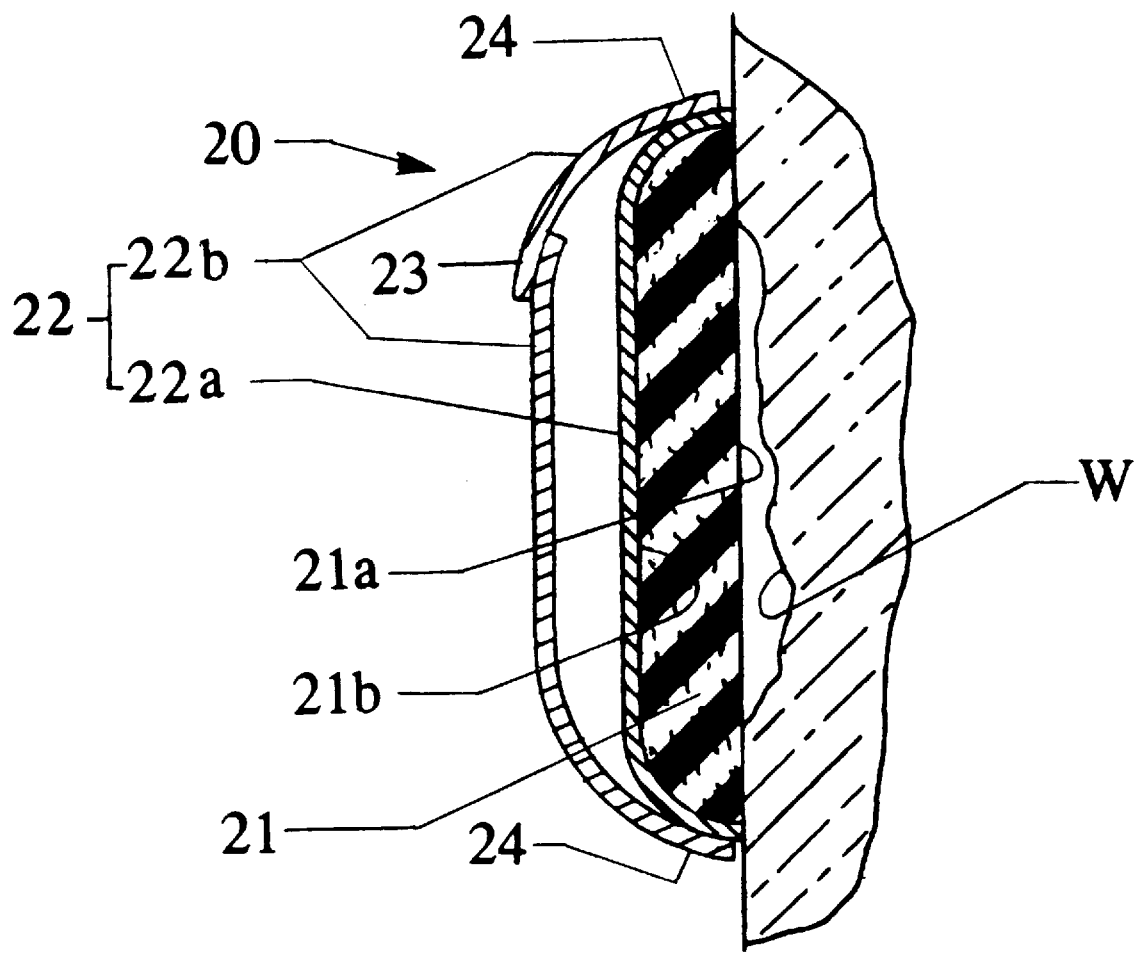
FIG. 2 is a side cross-sectional view of another embodiment of a wound dressing in accordance with the invention, and which permits replenishment of medicants without requiring removal of the dressing from the wound site.

Another embodiment, depicted in FIG. 2, permits the infusion of medicants into a dressing to replace those depleted during use, without requiring removal of the dressing from the wound site. A dressing, generally designated 20, and shown in contact with a wound W, includes a shaped mass 21 presenting an exterior surface configuration comprised of a wound contact surface 21a and an outwardly facing surface 21b. Means are provided, conveniently in the form of an enclosed envelope structure 22 comprised of film, fixed to outwardly disposed surface 21b of shaped mass 21, for retaining medicants instilled therein. The film envelope 22 is comprised of a fluid permeable layer 22a attached to, and in direct overlaid contact with, outwardly disposed surface 21b of shaped mass 21. Such fluid permeability may be accomplished conveniently, for example, by creation of a plurality of perforations in an otherwise fluid impermeable film. The remaining film which forms film envelope structure 22, and not in direct contact with shaped mass 21, is a fluid impermeable layer 22b. Fluid permeable layer 22a and fluid impermeable layer 22b are peripherally sealed to one another over sufficient edge portions 24 to permit retention of fluid medicants placed therebetween. For example, where shaped mass 21 and film envelope 22 are rectangular, fluid permeable layer 22a and fluid impermeable layer 22b are advantageously sealed along at least three sides to form a pocket-like configuration. By virtue of such structure, medicants may be instilled into the film envelope 22, which serves as a reservoir, from where they can then seep into shaped mass 21 through fluid permeable layer 22a disposed in a position interposed between shaped mass 21 and outermost fluid impermeable layer 22b, thereby replacing depleted medicants passing from the dressing into the wound. The degree of fluid permeability of fluid permeable layer 22a determines the rate at which fluid instilled into and contained within film envelope 22 is absorbed by shaped mass 21, thereby providing means for regulation of the medicant fluid uptake of shaped mass 21. Optionally, envelope structure 22 may include an entry flap 23 disposed along an upper edge thereof, scalable by for example reclosable contact adhesive. Many other alternative envelope configurations are envisioned, including for example a completely sealed envelope 22 into which medicants are instilled by use of a needle syringe in much the way contents of a ringer bag are currently accessed.

The embodiment depicted in FIG. 2 is useful for replenishment of any desired medicant, including germicidal material such as, for example, chlorhexadine gluconate, or chemotherepeutic agents for application to malignant ulcerations. Furthermore, the embodiment may be used particularly advantageously for replenishing iodine, where shaped mass 21 is a suitable material complexed with iodine, such as, for example, polyurethane foam. Following application of dressing 20 to wound site W, as iodine is released in therapeutically effective amounts to the moist wound, there is a color change from brown, to the original white color of the foam when the complexed iodine is completely exhausted. Upon such depletion, dressing 20 may be rejuvenated without requiring removal of same from the patient. Iodine instilled into film envelope 22 seeps into shaped mass 21 at a rate regulated by the permeability of fluid permeable layer 22a, complexing with the polyurethane foam or other suitable material of which it is comprised.

Suitable hydrophilic materials complexible with iodine and applicable to the above described embodiments are available from a variety of sources. For example, hydrophilic prepolymers are available from Hampshire Chemical Corporation, 55 Hayden Avenue, Lexington, Mass. 02173 under the trade name HYPOL. These prepolymers merely require the addition of water to form a hydrophilic open cell foam when mixed in the recommended manner. Premolded polyurethane foam is also available from Avitar, Inc., 250 Turnpike Street, Canton, Mass. 02021 and from E. N. Murray Company, Inc., 280 Boone Court, Plano, Tex. 75203. Extruded polyurethane foam, which is very hydrophilic and also suitable for use in accordance with the intended scope of the invention, is available from Madison Polymeric Engineering, 495 Ward Street Ext., Wallingford, Conn. 06492.

In accordance with a further embodiment of the invention, a wound dressing takes the form of a surgical drape, comprised of a hydrophilic film, and which may be adhered to skin to prevent contamination from airborne contaminants in, for example, an operating room. Such a drape is comprised of polyurethane film, or other suitable film substance capable of reversibly complexing with elemental iodine. It is noted that even highly cross-linked thermoset polyurethane complexes sufficiently with iodine to release iodine in quantities sufficient to establish an equilibrium of 5–10 ppm of free iodine in an aqueous medium, dependant on the degree of loading of the polyurethane.

The drape described above which provides a bacteriocidal barrier may be fabricated, for example, from a polyurethane film of desired widened dimensions, which is subsequently dipped in 2% aqueous iodine dissolved in 2.6% aqueous sodium iodide solution. The excess iodine solution is removed by passing the film through a ringer into a bath of continually changed deionized water. Washing is continued until the effluent is clear. The film is again passed through a ringer and air dried. When dry, one side of the film is coated with a contact cement suitable for use on human skin. Many such adhesives are available from The 3M Corporation and other companies serving the adhesive plaster market. The film is then adhered to a releasing film, and advantageously packaged to exclude air and extent shelf life. Although the drape need not be sterilized by virtue of the iodine contained therein, if so desired, such may be accomplished be exposure to gamma irradiation. Suitable hydrophilic films may be obtained, for example, from JPS Elastomerics Corp., 395 Pleasant Street, Northhampton, Mass. 01061-0658, or Miles Inc., Mobay Road, Pittsburgh, Pa. 15205-9741.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A wound dressing comprising:
    a shaped mass of a material, said material being included in a class capable of complexing with iodine, yet possessing reversible binding sites to allow release of free iodine in therapeutic concentrations;
    said shaped mass being sufficiently complexed with free iodine to render it bactericidal, virucidal, and fungicidal;
    said shaped mass including a wound contact surface, said wound contact surface including non-irritating surface configuration suitable for application to a wound site and a surface opposite said wound contact surface defining an outwardly disposed surface;
    a fluid permeable film coating disposed on said outwardly disposed surface and attached thereto; and
    a fluid impermeable film attached peripherally to said fluid permeable film coating disposed such that said fluid permeable film is interposed between said outwardly disposed surface and said fluid impermeable film, a combination of said fluid permeable film and said fluid impermeable film forming an envelope structure into which medicants are disposable without requiring removal of said wound dressing from said wound site, said fluid permeable film coating permitting passage of said medicants from said envelope to said shaped mass for absorption thereby.

2. A wound dressing as in claim 1, wherein said material is an open cell hydrophilic polyurethane foam.

3. A wound dressing as in claim 1, further comprising an organic polybasic acid for acidifying said shaped mass.

4. A wound dressing as in claim 1, wherein said material is a partially cross-linked polyalcoholic foam.

5. A wound dressing as in claim 1, wherein said material is a partially cross-linked polyvinyl alcohol polymer.

6. A wound dressing as in claim 1, wherein said material is a partially cross-linked cellulose polymer.

7. A wound dressing as in claim 1, wherein said material is acidified by one of an organic polybasic acid and a polycarboxylated polyvinyl resin.

8. A wound dressing as in claim 1, further comprising an entry flap permitting access to said reservoir and having a reclosable contact adhesive for sealing said reservoir.

9. A wound dressing as in claim 1, further comprising said reservoir being sealed and allowing said medicant to be disposed therein by means of a needle syringe.

10. A wound dressing, comprising:
    a shaped mass of a pliable and absorbent material, said shaped mass including a wound contact surface of non-irritating surface configuration suitable for application to a wound site and a surface opposite said wound contact surface defining an outwardly disposed surface;
    a fluid permeable film coating disposed on said outwardly disposed surface and attached thereto; and
    a fluid impermeable film attached peripherally to said fluid permeable film coating disposed such that said fluid permeable film is interposed between said outwardly disposed surface and said fluid impermeable film, a combination of said fluid permeable film and said fluid impermeable film forming an envelope structure defining reservoir into which medicants are disposable without requiring removal of said wound dressing from said wound site, said fluid permeable film coating permitting passage of said medicants from said reservoir to said shaped mass for absorption thereby.

11. A method for treating externally damaged tissue, comprising:
    applying a dressing to said damaged tissue, said dressing including a shaped mass of material, said material being included in a class capable of complexing with iodine, yet possessing reversible binding sites to allow the release of free iodine in therapeutic concentrations, said material having iodine complexed therewith, said shaped mass including a contact surface and an outwardly disposed surface opposite said contact surface;
    disposing said dressing with said contact surface in contact with said damaged tissue;
    permitting said dressing to remain in said contact with said damaged tissue over a period of time, said therapeutic concentrations of free iodine being released to said damaged tissue over said period of time of such contact; and
    adding a quantity of iodine solution to said shaped mass via said outwardly disposed surface while said dressing remains in said contact with said damaged tissue to replenish an amount of said iodine complexed with said material which is depleted by release of said therapeutic concentrations of free iodine to said damaged tissue over a portion of said period of time.

12. A wound dressing as in claim 11, wherein said material is a partially cross-linked polyalcoholic foam.

13. A wound dressing as in claim 11, wherein said material is a partially cross-linked polyvinyl alcohol polymer.

14. A wound dressing as in claim 11, wherein said material is a partially cross-linked cellulose polymer.

15. A wound dressing as in claim 11, wherein said material is acidified by one of an organic polybasic acid and a polycarboxylated polyvinyl resin.

16. The method according to claim 11, wherein said dressing further includes a fluid permeable film coating disposed on said outwardly disposed surface and attached thereto, and a fluid impermeable film sealably attached peripherally to said fluid permeable film coating disposed such that said fluid permeable film is interposed between said outwardly disposed surface and said fluid impermeable film, a combination of said fluid permeable film and said fluid impermeable film forming an envelope structure defining a reservoir into which medicants are disposable without requiring removal of said wound dressing, and said fluid permeable film coating permitting passage of said medicants from said reservoir to said shaped mass for absorption thereby.

17. The method according to claim 16, wherein said material is a hydrophilic open cell polyurethane foam, and said fluid permeable film coating is bondingly attached to said shaped mass.

18. A wound dressing as in claim 16, further comprising an entry flap permitting access to said reservoir and having a reclosable contact adhesive for sealing said reservoir.

19. A wound dressing as in claim 16, further comprising said reservoir being sealed and allowing said medicant to be disposed therein by means of a needle syringe.

20. A method for treating externally damaged tissue, comprising:
    providing a dressing including a shaped mass of material, said shaped mass including a contact surface and an outwardly disposed surface opposite said contact surface, a fluid permeable film coating disposed on said outwardly disposed surface and attached thereto, and a fluid impermeable film sealably attached peripherally to said fluid permeable film coating disposed such that said fluid permeable film is interposed between said outwardly disposed surface and said fluid impermeable film, a combination of said fluid permeable film and said fluid impermeable film forming an envelope structure defining a reservoir into which medicants are disposable without requiring removal of said wound dressing, and said fluid permeable film coating permitting passage of said medicants from said reservoir to said shaped mass for absorption thereby;

disposing said dressing with said contact surface in contact with said damaged tissue and disposing said medicants in said reservoir; and permitting said dressing to remain in said contact with said damaged tissue over a period of time, and replenishing said medicants in said reservoir to replace amounts released to said damaged tissue over said period of time of such contact.

\* \* \* \* \*